US011517227B2

United States Patent
Bebout et al.

(10) Patent No.: US 11,517,227 B2
(45) Date of Patent: *Dec. 6, 2022

(54) METHODS FOR MONITORING CARBOXYHEMOGLOBIN, INSPIRED AND EXPIRED CO2 AND CALIBRATION OF NON-INVASIVE ARTERIAL O2 SATURATION

(71) Applicants: Donald Edward Bebout, Cody, WY (US); William Leon Bednarski, Tahoma, CA (US)

(72) Inventors: Donald Edward Bebout, Cody, WY (US); William Leon Bednarski, Tahoma, CA (US)

( * ) Notice: Subject to any disclaimer, the term of this patent is extended or adjusted under 35 U.S.C. 154(b) by 379 days.

This patent is subject to a terminal disclaimer.

(21) Appl. No.: 16/942,755

(22) Filed: Jul. 29, 2020

(65) Prior Publication Data
US 2021/0007647 A1    Jan. 14, 2021

Related U.S. Application Data

(63) Continuation-in-part of application No. 15/612,933, filed on Jun. 2, 2017, now Pat. No. 10,772,562.

(51) Int. Cl.
| A61B 5/1455 | (2006.01) |
| A61B 5/00 | (2006.01) |
| A61B 5/0205 | (2006.01) |
| A61B 5/026 | (2006.01) |
| A61B 5/083 | (2006.01) |

(Continued)

(52) U.S. Cl.
CPC ........ *A61B 5/14552* (2013.01); *A61B 5/0205* (2013.01); *A61B 5/026* (2013.01); *A61B 5/6803* (2013.01); *A61B 5/7221* (2013.01); *A61B 5/024* (2013.01); *A61B 5/0816* (2013.01); *A61B 5/0836* (2013.01); *A61B 2503/22* (2013.01); *A61B 2560/0257* (2013.01); *A61B 2562/0219* (2013.01)

(58) Field of Classification Search
CPC ... A61B 5/14552; A61B 5/0205; A61B 5/026; A61B 5/6803; A61B 5/7221; A61B 5/024; A61B 5/0816; A61B 5/0836; A61B 2503/22; A61B 2560/0257; A61B 2562/0219; A61B 5/0077; A61B 5/18; A61B 5/489; A61B 5/02433; A61B 5/082
See application file for complete search history.

(56) References Cited

U.S. PATENT DOCUMENTS

2006/0264727 A1* 11/2006 Mannheimer ........ A61B 5/6814
600/340
2007/0221225 A1* 9/2007 Kutt ....................... A63B 23/18
128/204.23

* cited by examiner

*Primary Examiner* — Andrey Shostak
(74) *Attorney, Agent, or Firm* — Barry Choobin; Patent 360

(57) ABSTRACT

The present invention is directed to system and method for effectively monitoring critical respiratory parameters including $SpO_2$, PR, COHb, inspired $CO_2$, expired $CO_2$, respiration rate, respiration pattern, hyperventilation (hypocapnia), hypoventilation (hypercapnia), $CO_2$ contamination, and $CO_2$ rebreathing. The system according to the present invention comprises a pulse oximetry sensor and a $CO_2$ sensor connected to a central portable unit. The central unit comprising a barometer, an accelerometer, a capnography circuit, and a control unit. The control unit including the method for effectively monitoring critical respiratory parameters.

2 Claims, 4 Drawing Sheets

(51) Int. Cl.
*A61B 5/024* (2006.01)
*A61B 5/08* (2006.01)

METHODS FOR MONITORING CARBOXYHEMOGLOBIN, INSPIRED AND EXPIRED CO2 AND CALIBRATION OF NON-INVASIVE ARTERIAL O2 SATURATION

CROSS-REFERENCE TO RELATED APPLICATIONS

This application is a continuation-in-part of U.S. non-provisional patent application Ser. No. 15/612,933, filed Jun. 2, 2017, the contents of which are incorporated herein by reference in its entirety. This application also claims priority to the U.S. provisional patent application Ser. No. 62/829,213 filed Apr. 4, 2019, which is incorporated herein by reference in its entirety.

FIELD OF INVENTION

The embodiments herein generally relate to a method of in-flight pilot health monitoring, and particularly relate to a method for non-invasive monitoring of Carboxyhemoglobin, inspired and expired $CO_2$, calibration of non-invasive arterial oxygen saturation ($SpO_2$) of an aircraft pilot during in-flight conditions.

BACKGROUND

Insufficiency of oxygen in the blood is defined as hypoxemia, while an insufficiency of oxygen in the body tissue is defined as hypoxia. Hypoxemia can cause tissue hypoxia as blood may not be supplying enough oxygen to the tissue. Hypoxemia can also indirectly cause hypocapnia. Hypocapnia or hypocapnea, also known as hypocarbia is a state of reduced carbon dioxide in the blood. Hypocapnia can be induced by either a decrease in $CO_2$ production or an increase in $CO_2$ loss. During hypoxemia, to correct hypoxemia or hypoxia, the body is stimulated to breathe more leading to hyperventilation. Hyperventilation leads to increased expiration of $CO_2$ resulting in hypocapnia. Both hypoxemia and hypocapnia can have adverse effects on an individual. Both have different symptoms, however, hypocapnia may get undetected and there are virtually no mechanisms in the body to control hypocapnia except decreasing respiratory rate to regulate this loss.

Such a complex situation has been observed in pilots during flights. Hypoxia is the greatest single danger to a man at high altitudes, despite the importance of pressure and temperatures. When a pilot inhales air at high altitudes, there is not enough oxygen pressure to force adequate amounts of oxygen through the membranes of the lungs into the bloodstream, so that it can be carried to the tissues of the body. The function of various organs, including the brain, thereafter, begins getting impaired. The hypoxia scenario happens mainly during flights under high-G maneuvers sometimes results in fatal pilot conditions.

During the time frame from 2008-2012, the F-22 Raptor community experienced several unexplained hypoxia-like physiologic incidents including a cluster of four at one operating location that occurred during a 6-day period (Apr. 28-May 3, 2011). Following an F-22 fatal mishap on Nov. 16, 2010, that was reported as unexplained and the cluster of previously mentioned events, Air Combat Command (ACC) directed a fleet-wide F-22 strategic pause (grounding) from May 3, 2011-Sep. 21, 2011. In January 2012, an ACC-led F-22 Life Support Systems Task Force identified several root causes and potential contributors to the incidents. Testing in April-May 2012 at Brooks Air Force Base showed that one of the key contributors was a valve on the Combat Edge Vest (CEV), which is designed to pressurize the CEV during high-G maneuvers to improve pilot G-tolerance and provide counter chest pressure protection in the event of rapid decompression at high altitude. After May 3, 2011, F-22 Raptors were allowed back into service but with a very limited flight envelope. On Apr. 4, 2013, F-22's that had been equipped with emergency backup oxygen systems (ABOS—automatic backup oxygen system) were allowed back to unrestricted flight status. However, another 11-unexplained hypoxia-related incident occurred after the grounding showing that the rate had not changed.

The risks of hypoxia in high-performance fighter aircraft leading to Gravity Induced Loss of Consciousness (GLOC) have been known for years. More recently, the effectiveness and reliability of breathing systems within high-performance aircraft have been challenged by pilots as their primary daily concern. "Nothing scares Hornet (F-18) pilots more than losing oxygen—and it happens all the time." "It's like chasing a ghost," said Rear Admiral Mike "Nasty" Manazir, a career Navy pilot. "You can't figure it out, because the monitoring devices that do this are not on the airplane." Lives have been lost, expensive scarce aircraft damaged and destroyed, and mission effectiveness compromised through hypoxia and these idiopathic breathing issues in high-performance fighter aircraft.

Thus, the problems of oxygen deprivation and unexplained hypoxia-like physiologic events affect other aircraft besides the F-22, for example, the F-18 Hornet. Navy documents recorded 297 hypoxia-related incidents from May 2010 to October 2015, a number that is significantly rising. Possible reasons for the increase may include increased pilot awareness, less incentive to under-report and improved training of pilots to recognize hypoxia-related symptoms.

Thus, a need is appreciated for a monitoring system that could monitor critical respiratory parameters including Oxygen and Carbon dioxide.

In Congressional Hearings on F-22 Pilot Physiological Issues (Hearing Before the Subcommittee on Tactical Air and Land Forces of the Committee on Armed Services, House of Representatives, chaired by Representative Roscoe Bartlett with representatives from the Department of Defense, NASA, and others) the experts could not determine the cause of certain profoundly impactful symptoms because the same symptoms are shared by both hypoxia and hypocapnia. Mr. Bartlett: "Is it not true that, in large measure, the symptoms of hypoxia and hypocapnia are indistinguishable?" Air Force General Lyon: "Mr. Chairman that is what I found." The experts lack reliable objective data on which to base their judgments about the prevalence of these respiratory issues, their root causes, and the appropriate remediation. As a result, they tend to speculate including theories that pilots erroneously think they are hypoxic and thus breathe harder inducing hypocapnia. Mr. Bartlett: "If you think that you are hypoxic, the normal response is to try and get more oxygen . . . so you breathe deeper and maybe faster . . . you now drive down $CO_2$ and create the symptoms you were trying to avoid."

Following abbreviation have been used hereinafter to describe the invention:
$SpO_2$: Arterial oxygen saturation;
PR: pulse rate;
COHb: Carboxyhemoglobin;
$CO_2$: Carbon dioxide;
PO sensor: Pulse oximeter sensor;
AI: Altitude Indices;

VI: Vibration Indices;
GI: Gravitation Indices

SUMMARY OF THE INVENTION

Thus, the principal object of the present invention is to overcome the problem discussed above, by providing an system and method for effectively monitoring critical respiratory parameters including $SpO_2$, PR, COHb, inspired $CO_2$, expired $CO_2$, respiration rate, respiration pattern, hyperventilation (hypocapnia), hypoventilation (hypercapnia), $CO_2$ contamination, and $CO_2$ rebreathing.

It is another object of the present invention that the system and method provide the pilots with reliable accurate data to act upon and begin to address theory with fact.

It is still another object of the present invention that the system and method are resistant to motion artifacts, noise, and electromagnetic interference.

It is yet another object of the present invention that the system and method provides for reliable and accurate monitoring during the extreme conditions of high performance flight (high gravitational forces, reduced cabin pressures, extreme range of cabin temperatures and wearing required anti-gravity suit ensembles).

It is a further object of the present invention that the system and method provide non-invasive monitoring.

It is still a further object of the present invention that the system and method provide an alert upon detecting hypoxemic or hypoxic conditions in the pilot.

It is yet a further object of the present invention that the system and method provide an alert upon detecting hypocapnia in the pilot.

These and other objects and advantages of the embodiments herein will become readily apparent from the following detailed description taken in conjunction with the accompanied drawings.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
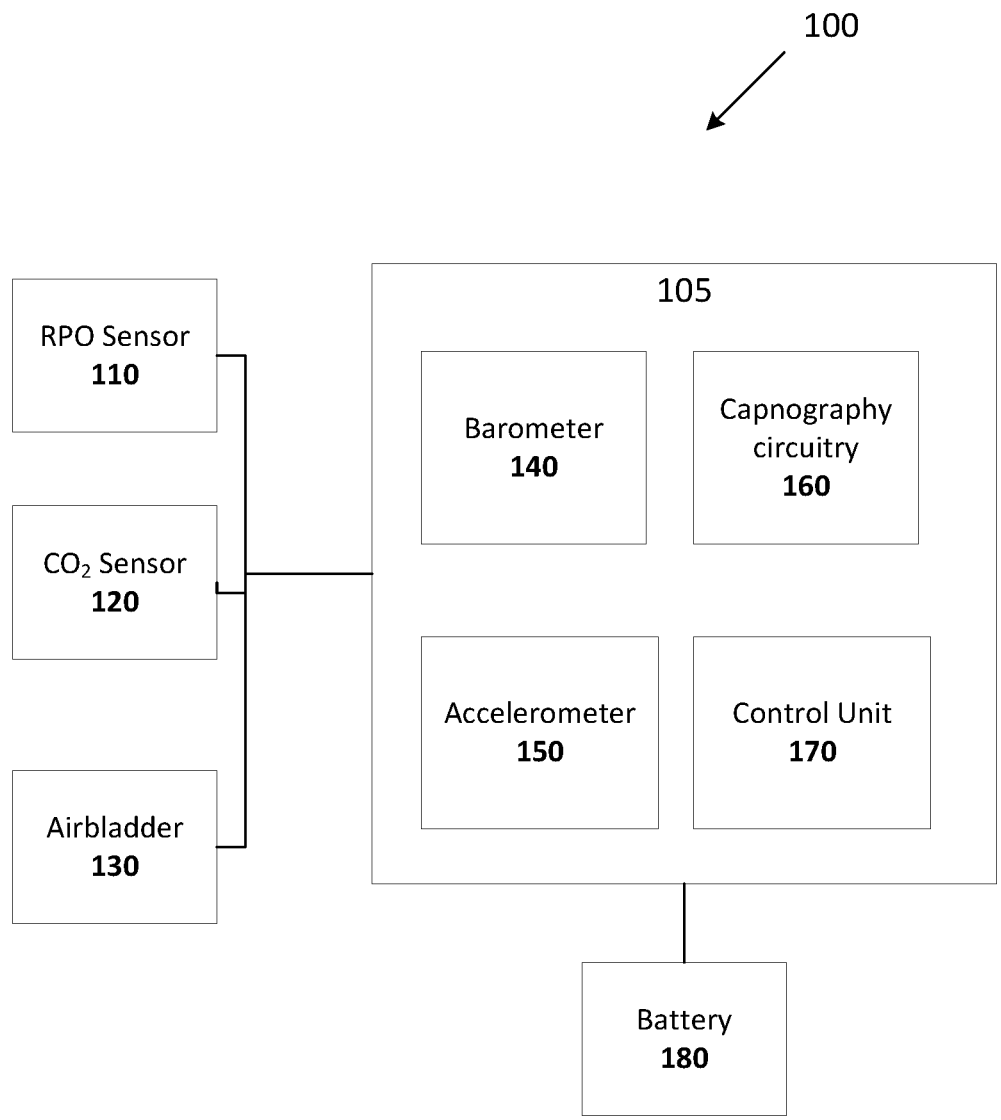
FIG. 1 is a block diagram showing the system, according to an embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as devices and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth in order to provide a thorough understanding of the subject innovation. It may be evident, however, that the claimed subject matter may be practiced without these specific details. In other instances, well-known structures and devices are shown in block diagram form in order to facilitate describing the subject innovation. Moreover, the drawings may not be to scale.

The present invention is directed to a system and method for effectively monitoring critical respiratory parameters including $SpO_2$, PR, COHb, inspired $CO_2$, expired $CO_2$, respiration rate, respiration pattern, hyperventilation (hypocapnia), hypoventilation (hypercapnia), $CO_2$ contamination, and $CO_2$ rebreathing. Now referring to FIG. 1 which shows an exemplary embodiment of the Enhanced Pulse Oximetry system (EPO) 100. The system 100 comprises a central unit 105, a PO sensor 110, a $CO_2$ sensor 120, and an airbladder 130. The central unit 105 further includes a barometer 110, a three-dimension accelerometer 150, a capnography circuitry 160, and a control unit 170. Further is shown in FIG. 1 is a battery powering the system 100.

The PO sensor 110 is configured to non-invasively determine $SpO_2$ and PR of a person. The PO sensor 110 can be configured in a headband of the pilot's helmet and held in place by a combination of padding, spring tension device and/or airbladder 130 connected to a pressure source that will be in concert with the anti-gravity systems, e.g., the anti-gravity suit ensemble (BRAG). Helmets that are equipped with a separate bladder, the sensor bladder can be connected to the system of separate bladder.

Figure 2:
FIG. 2 shows a PO sensor applied to a pilot and a central unit stored in the pocket of the pilot, according to an embodiment of the present invention.
Figure 3:
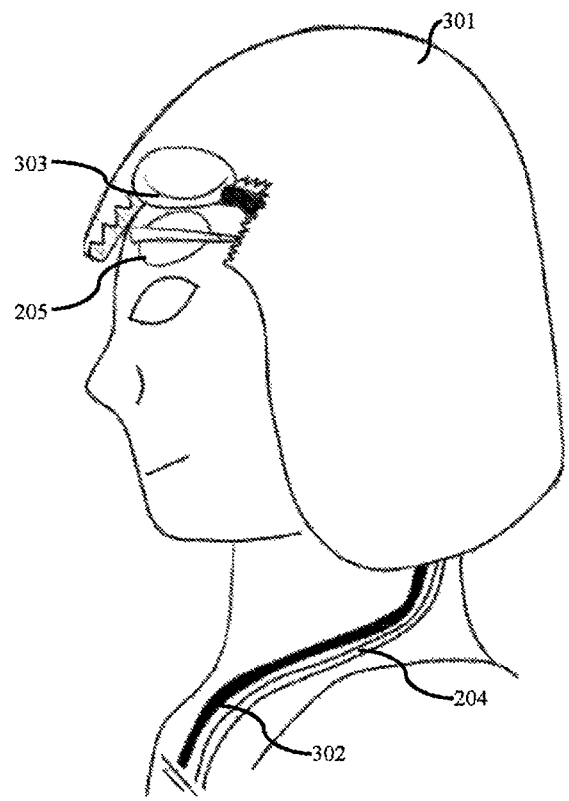
FIG. 3 shows the PO sensor and an airbladder, according to an embodiment of the present invention.
Figure 4:
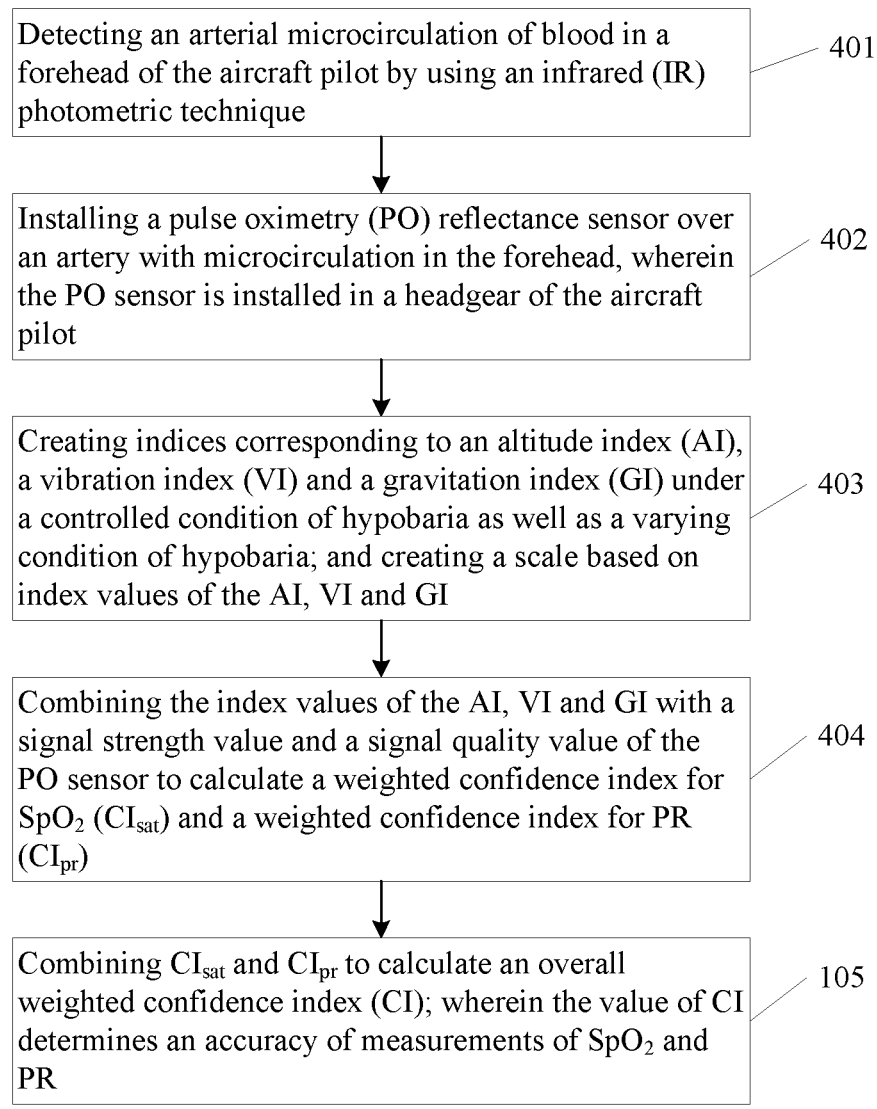
FIG. 4 is a flow chart showing a method, according to an embodiment of the present invention.

FIG. 2 shows the PO sensor 110 applied to a forehead portion of a pilot 210. The forehead has a unique microcirculation that is supplied from the internal carotid artery that has no vasoconstrictive properties. The rest of the head skin is supplied by the external carotid artery that does have vasoconstrictor properties. In fact, the forehead circulation is the only microcirculation in the entire skin that has no vasoconstrictor properties. Another advantage of monitoring on the forehead is that it provides a direct measure of brain or central arterial oxygenation as opposed to other sites that are far removed from vital organs and are the first sites to vasoconstrict when the body is faced with hypoxic stress. Illustrating with example of extreme cold and frostbite. The forehead is unaffected while fingers, toes, extremities, ears, and nose are the first to be compromised. A third advantage of monitoring on the forehead is the rapid response to changes in arterial oxygenation. Because the supraorbital microcirculation is supplied from the internal carotid artery, it directly reflects changes in brain or central arterial oxygenation. Lastly, it is advisable to avoid large arteries for sensor placement.

In one embodiment, the Infrared photometric technique can be used to a locate large arteries in the head's circulation. The IR photometric technique is well known method in the prior arts for determination of arterial flow and is easily understood by the ordinary person skilled in the art. The PO sensor 110 can be optimally positioned over the microcirculation for accurate performance. Moreover, the exact position of the PO sensor 110 can be determined by arterial blood accuracy studies that meet FDA Guideline PO standards under the novel conditions of hypobaria (equivalent altitudes of 0 to 25,000 ft), high vibration simulating tactical, transport and rotary aircraft and increased gravitational forces via centrifuge from 1 to 9 G's. Arterial blood $SaO_2$ and heart rate data can be compared to $SpO_2$ and PR values to determine accuracy under control conditions and varying conditions of hypobaria, vibration and increased gravitational forces. The numerical relationships between accuracy (bias, precision, root mean square of the differences and linear regression coefficients) under the above conditions can be used to calculate indices of AI, VI and GI.

The EPO system 100 contains a central unit 105 which can be portable and housed in a metallic or plastic casing. The central unit 105 can fit in a front pocket of the aviator's (aircraft pilot) vest or to be placed in cockpit or cabin as a stand-alone. The central unit 105 comprises a control unit 170 that contain all the algorithms for $SpO_2$, PR and COHb measurements as well as motion, vibration, pressure and acceleration tolerance, alarms and indices of signal strength and signal quality for all parameters. A barometer 140 or pressure manometer can also be provided for continuous monitoring of cabin pressure. A three-dimensional accelerometer 150 can also be housed in the central unit 105 that can be used for continuously monitoring direction and magnitude of G forces ($G_x$, $G_y$ and $G_z$). A capnography board 160 for integration of inspired and expired $CO_2$ for measurement and detection of respiratory rate and pattern, end tidal $CO_2$, hyperventilation, hypoventilation hypocapnia, hypercapnia, $CO_2$ contamination and $CO_2$ rebreathing. The system 100 can be powered by a rechargeable battery 180 that can be enclosed in the central unit 105. The control unit 170 is further configured for storing data acquired during functioning of the system 100. The control unit can be connected to an external computing system for transferring data to allow real-time data acquisition. The PO sensor 110 and the $CO_2$ sensor 120 can be connected to the control unit 170 through one or more electrical conduits.

The $CO_2$ sensor can be positioned directly into an aviator's mask of the pilot to detect inspired and expired $CO_2$, to generate continuous $CO_2$ breath-by-breath waveforms. This system and method according to the present invention can monitor Carboxyhemoglobin (COHb), inspired and expired $CO_2$ and calibration of non-invasive arterial oxygen saturation ($SpO_2$) for pilots and aircrew of tactical fighter, transport, and rotary aircraft. Monitoring can occur during all stages and conditions of flight including pre-flight checks, takeoff, mission flight and landing. Monitoring may be conducted during the extreme conditions of increased gravitational forces, reduced cabin pressures, wearing required anti-gravity aircrew flight equipment and during high vibration. The overall method for monitoring is to place a pulse oximetry (PO) sensor 110 above the eyebrow with the photo emitter and detector placed over the microcirculation fed by the supraorbital arterial supply. Exact placement will be individualized for each pilot using infra-red photographic technology to locate arteries in the forehead so they may be avoided to optimize sensor performance by placing the sensor over the desired microcirculation. Inspired and expired $CO_2$ can be monitored utilizing principles of Capnography for analysis of the data from the $CO_2$ sensor configured in the aviator's mask. Calibration of $SpO_2$ can be achieved by developing calibration curves for one or more combinations of red-light emitting diode wavelength (LED) and secondary emission. The calibration curve or curves can be embedded into the pulse oximetry algorithms and based on arterial blood studies conducted during hypoxia, CO exposure, hypobaria, high frequency vibration and increased gravitational forces.

The method further includes creation of indices corresponding to AI, VI, and GI under controlled conditions and varying conditions of hypobaria. The barometer, the accelerometer and the spring tension device can be used to measure the AI, VI, and GI. AI, VI and GI are indexes of values of altitude, vibration, and gravitation respectively which is easily comprehensible by an ordinary person skilled in the art. Also, a controlled condition of hypobaria relates to known medical practices of assessing the parameters (AI, VI and GI) during a flight simulation while the variable condition corresponds to measuring of parameters during an in-flight situation. Upon creation of the indices, a scale can be designed based on the values of the AI, VI and GI. The scale corresponds to the index values of AI, VI and GI and is shown as an understandable format over the pilot's HUD. The scale provides a relative reading to real-time readings of AI, GI and VI, so that a ground station and a pilot can understand the readings.

The values of AI, VI and GI are combined with a signal strength value and a signal quality value of the PO sensor 110 to calculate a weighted confidence index for $SpO_2$ ($CI_{sat}$) and a weighted confidence index for PR ($CI_{PR}$). The measured values of $CI_{sat}$ and $CI_{pr}$ can then be combined to calculate an overall weighted confidence index (CI). The value of the CI determines an accuracy of measurements of $SpO_2$ and PR. In one case, the scale is having a highest value of one that indicate an accurate functioning of the PO sensor. The lowest value can be zero that may indicate failure of the PO sensor. In one case, the indices can be scaled according to accuracy under the various conditions. For example, an index of 1.0 could be optimal conditions where there is no error and accuracy meet specifications (sea level, no vibration, 1 G). The index number will decrease below one as error increases until it reaches 0 which indicates PO failure or dropout of $SpO_2$ or PR values. These three novel indices can be combining with the existing measures of signal strength value (SS) and signal quality value (SQ) to develop an algorithm to calculate a final index of confidence (CI) of the $SpO_2$ and PR measurements based on numerical relations from arterial blood accuracy studies. The algorithm will weigh the values of AI, VI, GI, SS and SQ according to their effects on the accuracy measurements. A scale for CI can be computed that best fits the combined effects of AI, VI, GI, SS and SQ on accuracy.

According to one embodiment herein, the method further comprises a computer readable program to assess rapid changes in gravitational forces in multiple directions simultaneously. The changes affect an accuracy to calculate the vibration index (VI).

According to one embodiment herein, the method further comprises a computer readable program and a barometer to measure a cabin pressure. A change in a cabin pressure affects an accuracy to calculate the altitude index (AI).

According to one embodiment herein, the method further comprises a three-dimensional accelerometer and a computer readable program to measure gravitational forces in at-least three directions ($G_x$, $G_y$ and $G_z$. A magnitude of gravitational forces affects an accuracy to calculate the gravitational index (GI). The algorithms further enable calculation of motion and vibration tolerance, low perfusion performance, alarms and indices of signal strength and signal quality.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A system comprising:
   a housing;
   a control unit enclosed in the housing;
   a pulse oximetry (PO) sensor operably coupled to the control unit, the pulse oximetry sensor removably configured in a head gear and configured to be positioned over an arterial microcirculation of blood in a forehead of an aircraft pilot;
   a barometer operably coupled to the control unit; and
   an accelerometer operably coupled to the control unit,
   wherein the control unit is configured to:
      detect the arterial microcirculation by using an infrared (IR) photometric technique,
      receive arterial oxygen saturation ($SpO_2$) values, pulse rate (PR) values, a signal strength value and a signal quality value from the pulse oximetry sensor,
      create indices corresponding to an altitude index (AI), a vibration index (VI) and a gravitation index (GI) under a controlled condition of hypobaria as well as a varying condition of hypobaria,
      create a scale based on index values of the AI, VI and GI;
      combine the index values of the AI, VI and GI with the signal strength value and the signal quality value of the PO sensor to calculate a weighted confidence index for $SpO_2$ ($CI_{sat}$) and a weighted confidence index for PR ($CI_{pr}$); and
      combine $CI_{sat}$ and $CI_{pr}$ to calculate an overall weighted confidence index (CI);
   wherein the value of CI determines an accuracy of measurements of the $SpO_2$ values and the PR values.

2. The system of claim 1, wherein the system further comprises:
   a $CO_2$ sensor configured to be removably coupled with an aviator's mask of the pilot; and
   capnography circuitry operably coupled with the $CO_2$ sensor and the control unit, the capnography circuitry configured to estimate, based on $CO_2$ waveforms, respiratory rate, respiratory pattern, end tidal $CO_2$, hyperventilation, hypoventilation, hypocapnia, hypercapnia, $CO_2$ contamination and $CO_2$ rebreathing.

* * * * *